United States Patent [19]

Wade et al.

[11] 4,242,265

[45] Dec. 30, 1980

[54] INDOLYLALKYL ESTERS OF MERCAPTOALKANOIC ACIDS

[75] Inventors: Peter C. Wade, Pennington; Miguel A. Ondetti, Princeton, both of N.J.

[73] Assignee: E. R. Squibb & Sons, Inc., Princeton, N.J.

[21] Appl. No.: 2,430

[22] Filed: Jan. 10, 1979

Related U.S. Application Data

[63] Continuation-in-part of Ser. No. 815,472, Jul. 14, 1977, abandoned.

[51] Int. Cl.$^3$ .................. A61K 31/405; C07D 209/12
[52] U.S. Cl. .......................... 260/326.12 R; 548/341; 260/326.16; 260/326.13 C; 560/145; 562/598; 562/606; 424/274
[58] Field of Search .............................. 260/326.12 R

[56] References Cited

PUBLICATIONS

Hausler, et al., "Chem. Ber.", vol. 107, 1974, pp. 145-151.
Berse, et al., "J. Org. Chem.", vol. 27, 1962, pp. 3489-3495.
Vasilevskii, et al., "Zhur. Org. Khimii (transl.)", No. 2, 1970, pp. 244-249.

*Primary Examiner*—Donald G. Daus
*Assistant Examiner*—James H. Turnipseed
*Attorney, Agent, or Firm*—Lawrence S. Levinson; Burton Rodney

[57] ABSTRACT

New indolylalkyl esters of mercaptoalkanoic acids, and salts thereof, which have the general formula

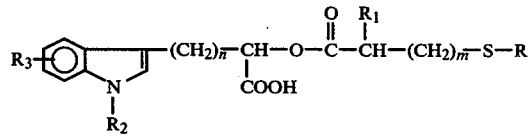

are useful as hypotensive agents.

17 Claims, No Drawings

INDOLYLALKYL ESTERS OF MERCAPTOALKANOIC ACIDS

This application is a continuation-in-part of application Ser. No. 815,472 filed July 14, 1977, by Miguel Angel Ondetti now abandoned.

BACKGROUND OF THE INVENTION

The prior application relates to carboxymethyl esters of mercaptopropanoic acids which have the formula

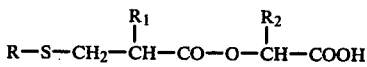

wherein R is hydrogen or lower alkanoyl; R₁ is hydrogen or lower alkyl; R₂ is hydrogen, lower alkyl, phenyl, phenyl-lower alkyl, 4-hydroxyphenyl-lower alkyl or indolyl-lower alkyl; and salts thereof.

In the parent application those compounds of the above formula wherein R₂ is indolyl-lower alkyl have been held to constitute a different invention. Upon additional experimentation, it has been found that a group of compounds of the above type, characterized by the presence of an indolyl-lower alkyl group, constitute a particularly interesting group as described below.

SUMMARY OF THE INVENTION

This invention relates to compounds which have the formula

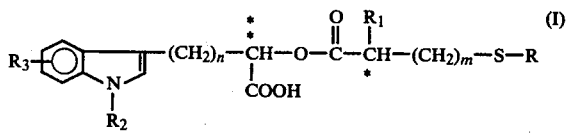

wherein
R is hydrogen, lower alkanoyl, benzoyl or

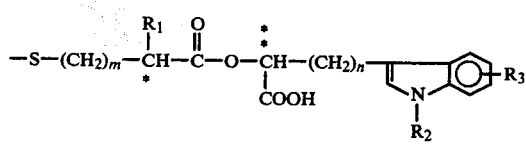

R₁ is hydrogen, lower alkyl or phenyl-lower alkyl;
R₂ is hydrogen or lower alkyl;
R₃ is hydrogen, halogen, hydroxy, nitro, lower alkoxy or lower alkylthio;
m and n each is 0, 1, 2 or 3 and to salts thereof.

The above compounds are useful as hypotensive agents.

DETAILED DESCRIPTION OF THE INVENTION

The lower alkyl groups are straight or branched chain hydrocarbon radicals having up to seven carbon atoms, e.g., methyl, ethyl, propyl, isopropyl, butyl, sec. butyl and the like. The C₁–C₄ and especially C₁–C₂ alkyl groups are preferred. The phenyl-lower alkyl, lower alkoxy and lower alkylthio groups include lower alkyl groups of the same type (with the same preferences expressed above).

The halogens are the four common halogens, chlorine and bromine being preferred.

The lower alkanoyl groups are the acyl radicals of the lower (C₂–C₇) fatty acids, e.g., acetyl, propionyl, butyryl, isobutyryl and the like. The members mentioned, and especially acetyl, are preferred.

Preferred members of the invention are those compounds of formula I wherein R is hydrogen or lower alkanoyl, especially hydrogen or acetyl; R₁ is hydrogen or lower alkyl, especially hydrogen or methyl; R₂ and R₃ each is hydrogen; m is 1; and n is 1.

The compounds of formula I are produced by acylation of an α-hydroxy acid having the formula

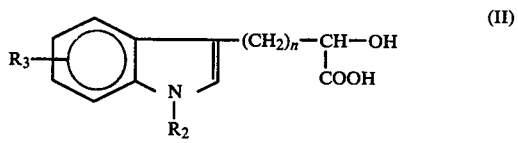

with an acid having the formula

by conventional esterification procedures.

One method comprises activating the acid of formula III with carbodiimidazole to form the acylimidazole intermediate having the formula

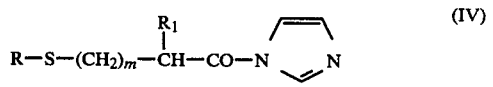

which is used without isolation. It is also preferred to form a product wherein R is lower alkanoyl, then treat the acyl derivative with ammonia, ammonium hydroxide or sodium hydroxide to obtain the product wherein R is hydrogen.

A preferred method comprises treating the acid of formula III, preferably wherein R is lower alkanoyl or benzoyl with an alkylchloroformate like methyl chloroformate in the presence of an organic base like triethylamine in an inert organic solvent like tetrahydrofuran, or the like then contacting this reaction mixture with the hydroxy acid of formula II. The acyl group can then be removed, if desired, as described above.

Another preferred method comprises treating the acid of formula III with thionyl chloride to yield the corresponding acid chloride, then reacting the acid chloride with the hydroxy acid of formula II in an inert solvent such as tetrahydrofuran in the presence of an acid acceptor, such as pyridine. The acyl group can be removed as described above.

The bis compounds or "dimers" formed when R is

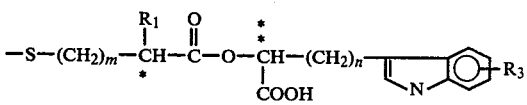

are obtained by oxidation of a compound of formula I wherein R is hydrogen, e.g., with an alcoholic solution of iodine.

The carbon atom marked with an asterisk in formula I is asymmetric if R₁ is other than hydrogen. The carbon atom marked with a double asterisk is always asymmetric. Thus the compounds with the asymmetric carbons exist as diastereoisomers or in racemic mixtures thereof. All of these are within the scope of the invention.

Some of the α-hydroxy acids of formula II are known compounds. Others may be prepared according to the following procedures. Other procedures are possible.

PROCEDURE I (n=1 to 3)

An $R_3$ substituted indole having the formula

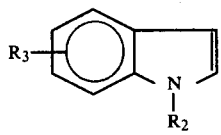

(VI)

(wherein $R_2$ is H) is acylated with an acyl chloride to give the acyl indole having the formula

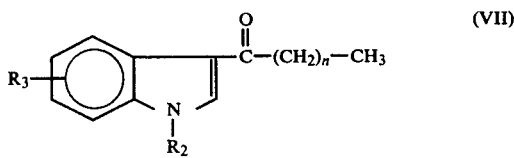

(VII)

in accordance with the teachings of Oddo et al., Gazz. Chim. Ital., 41 No. 1,234 (1911).

Treatment of VII with sulfur and morpholine [Willgerodt-Kindler reaction, Avramenko et al., Chem. Het. Cmpds., 698 (1973)] gives the terminal carboxy compound having the formula

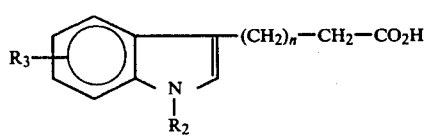

(VIII)

The lower alkyl group of $R_2$ may be optionally introduced by alkylating VI, VII or VIII (wherein $R_2$ is H) with an alkyl halide in hexamethylphosphoramide [Casnati et al., Chem. Ind. (Milan) 49 172 (1967)] to give the corresponding compound wherein $R_2$ is lower alkyl.

The α-hydroxy group may be introduced by treatment with 2 equivalents of lithium diisopropyl amide followed by oxidation with air [Moersch et al., Synthesis, 647 (1971)] or by bromination with bromine and phosphorus tribromide [Hell-Volhard-Zelinsky Reaction] followed by barium hydroxide hydrolysis [Johne et al., Z. Chem. 6, 149 (1966)] or by conversion to the cyanophosphonic ester having the formula

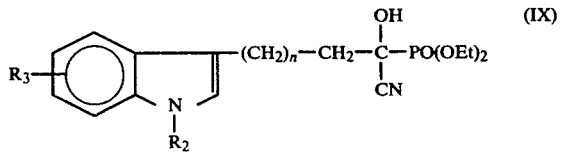

(IX)

and treatment of IX with potassium cyanide followed by hydrolysis according to the teachings of Okamoto et al., Kogyo Kagaku Zasshi 71 187 (1968) (Chem. Abstr. 69 35342), or by other methods known in the art.

In addition, many indolelactic acids may be prepared from the corresponding tryptophan compounds by fermentation with *Geotrichum candida* or by chemical means such as diazotization and hydrolysis or other procedures known in the art.

PROCEDURE II (n=0)

A procedure similar to that described in British Pat. No. 1,089,071 may be employed. The indole VI wherein $R_2$ is hydrogen or lower alkyl is treated with oxalyl chloride and a lower alkanol or benzyl alcohol to give the glyoxylic ester.

Reduction with sodium borohydride gives the glycolic ester; saponification of the ester under established conditions or catalytic hydrogenation (if it is a benzyl ester) gives the hydroxy acid.

The mercaptopropanoic acids of formula III can be produced as described in U.S. Pat. No. 4,053,651, Oct. 11, 1977, and No. 4,105,776, Aug. 8, 1978, e.g., by reacting a thioacid of the formula (X)

$R_4$—CO—SH wherein $R_4$ is lower alkyl, with an acrylic acid having the formula

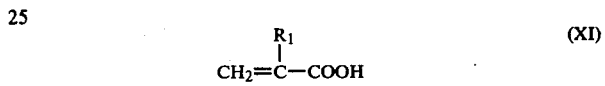

(XI)

$$CH_2=\overset{R_1}{\underset{|}{C}}-COOH$$

Other procedures known in the art may also be employed.

The $R_4$—CO group can be removed at this stage or later by treatment with ammonia or concentrated ammonium hydroxide as described above.

The compounds of formula I form the common (basic) salts of carboxylic acids, e.g., by reaction with inorganic or organic bases. Such well known salts include ammonium salts, alkali metal salts like sodium and potassium salts, alkaline earth metal salts like calcium and magnesium salts, salts with organic bases, e.g., dicylcohexylamine, benzathine, hydrabamine and N-methyl-D-glucamine salts. Since some of the compounds of formula I are not readily obtainable as crystalline substances with well defined melting points, the salts (which are not necessarily physiologically acceptable) provide means to isolate and characterize the product by conventional techniques.

Additional experimental details can be found in the illustrative examples below.

The compounds of this invention are angiotensin converting enzyme inhibitors and are useful as hypotensive agents, particularly for the reduction of renin-angiotensin dependent hypertension. By administering a composition containing one or a combination of angiotensin converting enzyme inhibitors of this invention to a hypertensive mammal, e.g., rats, mice, cats, dogs, etc. it intervenes in the renin→angiotensinogen→angiotensin→angiotensin II sequence and the hypertension is reduced or alleviated.

A single dose, or preferably two to four divided daily doses, provided on a basis of about 1 to 1000 mg. per kilogram per day and especially about 10 to 100 mg. per kilogram per day is appropriate to bring about a reduction in elevated blood pressure. The animal model experiments described by Engel et al., Proc. Soc. Exp. Biol. Med. 143, 483 (1973) provide a valuable guide.

The composition is preferably administered orally, but it can also be administered subcutaneously, intramuscularly, intravenously or intraperitoneally. The compound or compounds of formula I can be formulated as tablets, capsules or elixirs for oral administration. Sterile solutions or suspensions can be used for parenteral use.

About 20 to 1000 mg. of a compound or compounds of formula I or physiologically acceptable salt thereof can be compounded with a physiologically acceptable vehicle, carrier, excipient, binder, preservative, stabilizer, flavor, etc., in a conventional unit dosage form as called for by accepted pharmaceutical practice. The amount of active substance is selected so as to provide a dosage in the range indicated.

The following examples are illustrative of the invention. The examples from the parent application are also included herein in order to provide additional details of experimental methodology. All temperatures are in degrees Celsius.

EXAMPLE 1

O-(3-Acetylthiopropanoyl)glycolic Acid 3-(Acetylthio)propanoic acid (2.96 g.) and 1,1'-carbonyldiimidazole (3.24 g.) are dissolved in 20 ml. of dry tetrahydrofuran with stirring at room temperature. After twenty minutes, a solution of glycolic acid (1.52 g.) and 2.80 ml. of triethylamine in 15 ml. of tetrahydrofuran are added. The reaction mixture is stored overnight at room temperature. The tetrahydrofuran is removed in vacuo, the crude residue taken up into ethyl acetate, washed with 1 N hydrochloric acid and three times with water, dried over magnesium sulfate and the O-(3-acetylthiopropanoyl)glycolic acid is concentrated to dryness in vacuo, yield 3.9 g. This is dissolved in ether and dicyclohexylamine is added. The dicyclohexylamine salt precipitates, yield 2.85 g., m.p. 150°–157°. The salt is converted to the free acid by adding to ethyl acetate and adding 10% potassium bisulfate solution, yield 1.5 g.

EXAMPLE 2

O-(3-Mercaptopropanoyl)glycolic Acid

O-(3-acetylthiopropanoyl)glycolic acid from Example 1 (1.3 g.), under a blanket of argon is treated for fifteen minutes with a cold solution of 7 ml. of water and 7 ml. of concentrated ammonium hydroxide. This is chilled, acidified with concentrated hydrochloric acid and extracted into ethyl acetate, yield: 1.2 g. This product O-(3-mercaptopropanoyl)-glycolic acid is chromatographed on DEAE Sephadex A25 (Polidextrane anion exchange resin) with a linear gradient of ammonium bicarbonate. The desired fractions (45–70; U.V. peak at 254 nm.) are pooled, concentrated and lyophilized. This ammonium salt of O-(3-mercaptopropanoyl)glycolic acid is converted to the free acid by treatment with Dowex 50WX2 cation exchange resin, yield 320 mg. The O-(3-mercaptopropanoyl)glycolic acid is converted to the dicyclohexylamine salt by dissolving in ether and precipitating by the addition of dicyclohexylamine, m.p. 143°–144°.

EXAMPLE 3

O-[3-(Acetylthio)-2-Methylpropanoyl]Glycolic Acid

A mixture of thioacetic acid (50 g.) and methacrylic acid (40.7 g.) is heated on the steam bath for one hour and then stored at room temperature for 18 hours. After confirming by nmr spectrocopy that complete reaction of the methacrylic acid has been achieved, the reaction mixture is distilled in vacuo and the desired 3-acetylthio-2-methylpropanoic acid is separated in the fraction with boiling point 128.5°–131° (2.6 mmHg.), yield 64 g.

3-Acetylthio-2-methylpropanoic acid (6.48 g.) is taken into 40 ml. of dry tetrahydrofuran. To this 1,1'-carbonyldiimidazole (0.48 g.) is added and stirred for 30 minutes at room temperature. Glycolic acid (6.08 g.) and 11.2 ml. of triethylamine in 60 ml. of dry tetrahydrofuran are added. After several minutes, the imidazole salt of glycolic acid begins to come out of solution. The reaction is permitted to run overnight at room temperature. The crystalline salt is filtered and the filtrate concentrated to dryness in vacuo. The residue is taken up into ethyl acetate, washed with 1 N hydrochloric acid and three times with water, dried over magnesium sulfate and concentrated to dryness in vacuo. This product is converted to its dicyclohexylamine salt by dissolving in ether/hexane and precipitating by the addition of dicyclohexylamine. The salt is recrystallized from ether, m.p. 120°–122°. This salt is then converted to the free acid, O-[3-(acetylthio)-2-methylpropanoyl]glycolic acid, by adding to ethyl acetate, adding 10% potassium bisulfate solution, then crystallizing from ethyl/hexane, yield 2.96 g., m.p. 50°–51°.

EXAMPLE 4

O-(DL-3-Mercapto-2-Methylpropanoyl)Glycolic Acid

O-[3-(Acetylthio)-2-methylpropanoyl]glycolic acid (1.5 g.) is placed under a blanket of argon. To this a cold solution of 7.5 ml. of concentrated ammonium hydroxide and 7.5 ml. of water is added and the mixture is stored for 15 minutes at room temperature. This is then acidified with concentrated hydrochloric acid and extracted with ethyl acetate, yield 1.3 g. This product is dissolved in ether/hexane and dicyclohexylamine is added to precipitate the dicyclohexylamine salt, yield 2.24 g., m.p. 96°–98°. A 1.9 g. aliquot of the salt is converted to the free O-(DL-3-mercapto-2-methylpropanoyl)glycolic acid by adding to ethyl acetate and adding 10% potassium bisulfate solution, yield 0.9 g. The product is a heavy oil which is chromatographed in silica gel (benzene 7:2 acetic acid), $R_f+0.49$, traces $R_f=0.32$ and 0.57.

EXAMPLE 5

O-L-[3-(Acetylthio)propanoyl]-3-Phenyllactic Acid 3-(Acetylthio)propanoic acid (1.48 g.) is added to 10 ml. of dry tetrahydrofuran with stirring. To this 1,1'-carbonyldiimidazole (1.62 g.) is added and the mixture stirred for twenty minutes at room temperature. L-(−)-3-phenyllactic acid (1.66 g.) is added in a solution of 7.5 ml. of dry tetrahydrofuran and 1.4 ml. of triethylamine. The reaction mixture is stored overnight at room temperature. The tetrahydrofuran is removed in vacuo, the residue is taken up into ethyl acetate, washed with 1 N hydrochloric acid, three times with water, dried over magnesium sulfate and concentrated to dryness in vacuo, yield 2.8 g. The O-L-[3-(acetylthio)propanoyl]-3-phenyllactic acid is purified on a silica gel column, eluting with benzene 7:1 acetic acid, yield 1.7 g.

EXAMPLE 6

O-L-(3-Mercaptopropanoyl)-3-Phenyllactic Acid

To 1.5 g. of O-L-[3-(acetylthio)propanoyl]-3-phenyllactic acid a solution of 7.5 ml. of water and 7.5 ml. of concentrated ammonium hydroxide is added under an argon blanket. After fifteen minutes, the reaction mixture is chilled, acidified with concentrated hydrochloric acid and extracted into ethyl acetate, yield 1.1 g. The product, O-L-(3-mercaptopropanoyl)-3-phenyllactic acid is purified on a silica gel column, eluting with benzene 14:1 acetic acid, yield 357 mg. A small portion of the semi-solid product is converted to its dicyclohexylamine salt by dissolving in ether/hexane and precipitating with dicyclohexylamine, m.p. 100°.

EXAMPLE 7

O-DL-(3-Acetylthiopropanoyl)-3-Indolelactic Acid

By substituting DL-3-indolelactic acid for the L-β-phenyllactic acid in the procedure of Example 5, O-DL-(3-acetylthiopropanoyl)-3-indolelactic acid is obtained.

EXAMPLE 8

O-DL-(3-Mercaptopropanoyl)-3-Indolelactic Acid

By substituting O-DL-(3-acetylthiopropanoyl)-3-indolelactic acid for the O-L-(3-acetylthiopropanoyl)-3-phenyllactic acid in the procedure of Example 6, O-DL-(3-mercaptopropanoyl)-3-indolelactic acid is obtained.

EXAMPLE 9

O-DL-(3-Mercapto-2-Methylpropanoyl)-3-Indolelactic Acid

By substituting 3-indolelactic acid for the glycolic acid in the procedure of Example 3 and then submitting the product to the procedure of Example 4, O-DL-[3-(acetylthio)-2-methylpropanoyl]-3-indolelactic acid and O-DL-(3-mercapto-2-methylpropanoyl)-3-indolelactic acid are obtained.

EXAMPLE 10

O-L-(3-Mercaptopropanoyl)lactic Acid

By substituting L-lactic acid for the glycolic acid in the procedure of Example 1 and then submitting the product to the procedure of Example 2, O-L-(3-acetylthiopropanoyl)lactic acid and O-L-(3-mercaptopropanoyl)lactic acid are obtained.

EXAMPLE 11

O-L-(3-Mercaptopropanoyl)-α-Hydroxyisocaproic Acid

By substituting L-α-hydroxyisocaproic acid [Winitz, et al., J.Am. Chem. Soc. 78, 2423 (1956)] for the glycolic acid in the procedure of Example 1 and then submitting the product to the procedure of Example 2, O-L-(3-acetylthiopropanoyl)-α-hydroxy-isocaproic acid and O-L-(3-mercaptopropanoyl)-α-hydroxy-isocaproic acid are obtained.

EXAMPLE 12

O-L-(3-Acetylthiopropanoyl)-3-(p-tert-butoxyphenyl)-lactic Acid

By substituting 3-(p-tert-butoxyphenyl)lactic acid [obtained from O-tert-butyl-L-tyrosine by the procedure described by H. D. Dakin and H. W. Dudley in J. Biol. Chem., 18, 29 (1914) for the preparation of 3-L-phenyllactic acid] for the 3-L-phenyllactic acid in the procedure of Example 5, O-L-(3-acetylthiopropanoyl)-3-(p-tert-butoxyphenyl)lactic acid is obtained.

EXAMPLE 13

O-L-(3-Mercaptopropanoyl)-3-p-Hydroxyphenyllactic Acid

O-L-(3-acetylthiopropanoyl)-3-(p-tert-butoxyphenyl)lactic acid (1.8 g.) is dissolved in trifluoroacetic acid (15 ml.) and the solution is stored at room temperature for one hour. After removing the trifluoroacetic acid in vacuo, the residue is dissolved in a mixture of water (7.5 ml.) and concentrated ammonium hydroxide (7.5 ml.) under an argon blanket. After fifteen minutes, the reaction mixture is chilled, acidified with concentrated hydrochloric acid and extracted with ethyl acetate. The organic layer is concentrated in vacuo to yield O-L-(3-mercaptopropanoyl)-3-hydroxyphenyllactic acid.

EXAMPLE 14

O-(3-Mercaptopropanoyl)mandelic Acid

By substituting mandelic acid for the L-3-phenyllactic acid in the procedure of Example 5, and then submitting the product to the procedure of Example 6, O-(3-acetylthiopropanoyl)mandelic acid and O-(3-mercaptopropanoyl)mandelic acid are obtained.

EXAMPLE 15

O-DL-(3-Acetylthiopropanoyl)-3-Indolelactic Acid

To 6.66 g. (0.045 mol.) of 3-(acetylthio)-propanoic acid in 250 ml. of dry tetrahydrofuran in an ice/acetone (−5°) bath is added 4.55 g. (0.045 mol.) of triethylamine followed by 4.25 g. (0.045 mol.) of methyl chloroformate (dropwise over 5 minutes). A copious precipitate of triethylamine hydrochloride forms immediately. After the mixture is stirred for 30 minutes, 6.0 g. (0.029 mol.) of DL-indolelactic acid in 50 ml. of dry tetrahydrofuran is added all at once. The mixture is stirred for 3 hours at 0°, then allowed to stand in the refrigerator (0°) overnight. The reaction mixture is poured into 1 liter of ice cold saturated sodium chloride solution, covered with 500 ml. of ethyl acetate and stirred. The layers are separated and the aqueous layer is washed with two 250 ml. portions of ethyl acetate (pH of aqueous is 5.5). The ethyl acetate portions are combined, dried ($Na_2SO_4$) and stripped to yield 15 g. of residue. This material is then taken up in 500 ml. of ethyl acetate and extracted with 3×100 ml. of cold saturated sodium bicarbonate solution. The aqueous solution is acidified with concentrated hydrochloric acid to pH 1 and reextracted with ethyl acetate. The organic solution is dried ($Na_2SO_4$) and evaporated to dryness to yield 8.8 g. of residue. The 8.8 g. of material is chromatographed on 400 g. of silica gel with 8:2 benzene:acetic acid. The pure fractions are combined and stripped to yield 7.3 g (76%) of O-DL-(3-acetylthiopropanoyl)-3-indolelactic acid.

EXAMPLE 16

O-DL-(3-Mercaptopropanoyl)-3-Indolelactic Acid 5.9 g. (0.018 mol.) of the product of Example 14 is dissolved in a mixture of 25 ml. of concentrated ammonium hydroxide and 25 ml. of water and stirred (under Argon) for 20 minutes. The mixture is acidified with concentrated hydrochloric acid and extracted with ethyl acetate, which is, in turn, dried (Na$_2$SO$_4$) and stripped to yield 5.0 g. (97% crude) of residue. This material is chromatographed on 400 g. of silica gel with 9:1 benzene:acetic acid. The pure fractions are combined and stripped to yield 5.5 g of residue (containing some solvent) which solidifies (m.p. 54–56) on standing in the freezer. 3.86 g. (0.013 mol.) of the residue is dissolved in 300 ml. of ether and treated with 2.38 g. (0.0137 mol.) of dicyclohexylamine in 100 ml. of ether. The resulting clear solution is allowed to stand overnight under argon at room temperature. The resulting dicyclohexylamine salt (5.5 g., m.p. 152–154°) is filtered off and partitioned between water pH 1 and ethyl acetate. After 30 minutes, the layers are separated and the ethyl acetate layer is dried (Na$_2$SO$_4$) and stripped to yield an oil that slowly solidifies after the addition of seed crystals. Drying overnight at room temperature (1 torr) gives a solid, m.p. 53–55°. room temperature (1 torr) gives a solid, m.p. 53–55°. Drying overnight at 40° (1 torr) yields 3.3 g. of analytically pure O-DL-(3-mercaptopropanoyl)-3-indolelactic acid as a tacky, glassy solid.

Anal. Calc'd. for C$_{14}$H$_{15}$NO$_4$S: C, 57.32; H, 5.15; N, 4.78; S, 10.93. Found; C, 57.35; H, 5.29; N, 4.60; S, 10.65; SH 100%

The product is non-crystalline and has no melting point, but softens and starts to flow at 54–56°. It forms crystalline or semicrystalline solvates with acetic acid and ethyl acetate and chloroform. They all melt in the 53–56° range.

An aliquot of free acid in ether is treated with one equivalent of dicyclohexylamine in ether, as above, to yield the dicyclohexylamine salt, m.p. 151°–153°.

Anal. Calc'd for C$_{26}$H$_{38}$N$_2$O$_4$S: C, 65.79; H, 8.07; N, 5.90; S, 6.75 Found: C, 65.57; H, 8.12; N, 5.72; S, 6.51.

EXAMPLE 17 to 31

By substituting the hydroxy acid shown in Column I of Table A set out below for DL-indolelactic acid and substituting the thio acid shown in Column II for 3-(acetylthio)propanoic acid in the procedure of Example 15, the final products shown in Column III are obtained.

TABLE A

| | Column I | | | Column II | | |
|---|---|---|---|---|---|---|
| | R$_3$—[indole, N-R$_2$]—(CH$_2$)$_n$—CH(OH)—COOH | | | R—S—(CH$_2$)$_m$—CH(R$_1$)—COOH | | |
| | R$_3$ | R$_2$ | n | R | m | R$_1$ |
| 17 | H | H | 3 | CH$_3$CO | 1 | H |
| 18 | 5-Cl | H | 1 | C$_6$H$_5$—CO | 0 | H |
| 19 | 5-Br | H | 1 | C$_4$H$_9$CO | 1 | C$_2$H$_5$ |
| 20 | 5-OH | C$_2$H$_5$ | 1 | C$_2$H$_5$CO | 2 | H |
| 21 | 5-OC$_2$H$_5$ | H | 1 | C$_3$H$_7$CO | 3 | H |
| 22 | 4-SCH$_3$ | CH$_3$ | 1 | CH$_3$CO | 1 | H |
| 23 | 4-NO$_2$ | H | 1 | C$_4$H$_9$CO | 0 | H |
| 24 | H | H | 1 | CH$_3$CO | 2 | H |
| 25 | H | CH$_3$ | 0 | CH$_3$CO | 1 | H |
| 26 | H | CH$_3$ | 2 | C$_2$H$_5$CO | 1 | H |
| 27 | H | CH$_3$ | 0 | C$_6$H$_5$—CO | 1 | H |
| 28 | H | C$_2$H$_5$ | 1 | CH$_3$CO | 1 | C$_4$H$_9$ |
| 29 | H | H | 1 | CH$_3$CO | 1 | C$_6$H$_5$—CH$_2$— |
| 30 | 5-F | H | 1 | CH$_3$CO | 1 | C$_6$H$_5$—CH$_2$ |
| 31 | 6-F | H | 1 | C$_2$H$_5$CO | 1 | C$_6$H$_5$—CH$_2$CH$_2$— |

| | Column III | | | | | |
|---|---|---|---|---|---|---|
| | R$_3$—[indole, N-R$_2$]—(CH$_2$)$_n$CH(COOH)—O—C(=O)—CH(R$_1$)—(CH$_2$)$_m$—S—R | | | | | |
| | R$_3$ | R$_2$ | n | R | m | R$_1$ |
| 17 | H | H | 3 | CH$_3$CO | 1 | H |
| 18 | 5-Cl | H | 1 | C$_6$H$_5$—CO | 0 | H |
| 19 | 5-Br | H | 1 | C$_4$H$_9$CO | 1 | C$_2$H$_5$ |
| 20 | 5-OH | C$_2$H$_5$ | 1 | C$_2$H$_5$CO | 2 | H |
| 21 | 5-OC$_2$H$_5$ | H | 1 | C$_3$H$_7$CO | 3 | H |
| 22 | 4-SCH$_3$ | CH$_3$ | 1 | CH$_3$CO | 1 | H |
| 23 | 4-NO$_2$ | H | 1 | C$_4$H$_9$CO | 0 | H |
| 24 | H | H | 1 | CH$_3$CO | 2 | H |
| 25 | H | CH$_3$ | 0 | CH$_3$CO | 1 | H |
| 26 | H | CH$_3$ | 2 | C$_2$H$_5$CO | 1 | H |

TABLE A-continued

| | | | | | | |
|---|---|---|---|---|---|---|
| 27 | H | $CH_3$ | 0 | ⌬—CO | 1 | H |
| 28 | H | $C_2H_5$ | 1 | $CH_3CO$ | 1 | $C_4H_9$ |
| 29 | H | H | 1 | $CH_3CO$ | 1 | ⌬—$CH_2$— |
| 30 | 5-F | H | 1 | $CH_3CO$ | 1 | ⌬—$CH_2$— |
| 31 | 6-F | H | 1 | $C_2H_5CO$ | 1 | ⌬—$CH_2CH_2$— |

EXAMPLES 32 to 46

By submitting the products of Examples 17 to 31 shown in Column III of Table A to the procedure of Example 16, the final products corresponding to the products of Examples 17 to 31 wherein R is hydrogen are obtained.

EXAMPLE 47

Disulfide of O-DL-(3-Mercaptopropanoyl)-3-Indolelactic Acid

O-DL-(3-Mercaptopropanoyl)-3-indolelactic acid from Example 16 (4 g.) is dissolved in 67 ml. of water and the pH adjusted to 6.5 with 1 N sodium hydroxide. To this a total of 27.8 ml. of 0.5 M iodine solution (95% EtOH) is added dropwise while maintaining a pH of 5.5 to 6.5 with 1 N sodium hydroxide. After 15 minutes a trace of excess iodine is discharged with dilute sodium thiosulfate. The reaction mixture is concentrated in vacuo, acidified with concentrated HCl and extracted with ethyl acetate. The organic layer is dried over magnesium sulfate and concentrated to dryness in vacuo to yield the compound of the title.

EXAMPLE 48

O-L-(D-3-Acetylthio-2-methylpropanoyl)-3-indolelactic acid

Following the procedure of Example 15, but substituting L-indolelactic acid for DL-indolelactic acid and substituting D-3-acetylthio-2-methylpropanoic acid for 3-acetylthiopropanoic acid, the title compound is obtained.

EXAMPLE 49

O-L-(D-3-Mercapto-2-methylpropanoyl)-3-indolelactic acid

Submitting the product of Example 48 to the procedure of Example 16, gives the title compound.

What is claimed is:

1. A compound of the formula

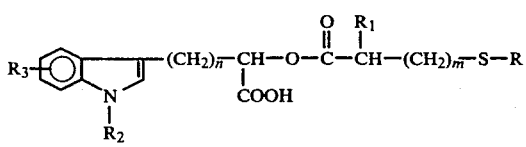

wherein

R is hydrogen, lower alkanoyl, benzoyl or

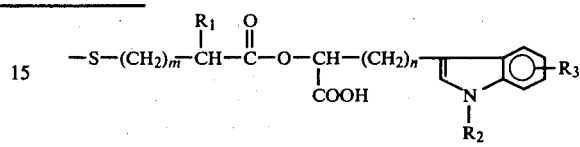

$R_1$ is hydrogen, lower alkyl or phenyl-lower alkyl;
$R_2$ is hydrogen or lower alkyl;
$R_3$ is hydrogen, halogen, hydroxy, nitro, lower alkoxy or lower alkylthio;
m and n each is 0, 1, 2 or 3 and pharmaceutically acceptable basic salts thereof.

2. A compound as in claim 1 wherein $R_2$ is hydrogen.
3. A compound as in claim 1 wherein $R_2$ and $R_3$ are hydrogen.
4. A compound as in claim 1 wherein m is 1.
5. A compound as in claim 1 wherein R is hydrogen or lower alkanoyl.
6. A compound as in claim 1 wherein R is hydrogen or lower alkanoyl; $R_1$ is hydrogen or lower alkyl; $R_2$ and $R_3$ each is hydrogen; m is 1 and n is 1.
7. A compound as in claim 1 wherein R is hydrogen or acetyl, $R_1$ is hydrogen or methyl; $R_2$ and $R_3$ each is hydrogen; m is 1; and n is 1.
8. A compound as in claim 1 wherein R, $R_2$ and $R_3$ each is hydrogen.
9. A compound as in claim 1 wherein R is

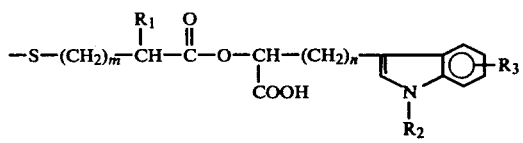

10. A compound as in claim 1 wherein R is hydrogen.
11. A compound as in claim 1 wherein R is lower alkanoyl.
12. A compound as defined in claim 1 having the name O-DL-(3-acetylthiopropanoyl)-3-indolelactic acid.
13. A compound as defined in claim 1 having the name O-DL-(3-mercaptopropanoyl)-3-indolelactic acid.
14. A compound as defined in claim 1 having the name O-L-(D-3-acetylthio-2-methylpropanoyl)-3-indolelactic acid.
15. A compound as defined in claim 1 having the name O-L-(D-3-mercapto-2-methylpropanoyl)-3-indolelactic acid.
16. A compound as defined in claim 1 having the name O-DL-(3-acetylthiopropanoyl)-1-methyl-3-indoleglycolic acid.
17. A compound as defined in claim 1 having the name O-DL-(3-mercaptopropanoyl)-1-methyl-3-indoleglycolic acid.

* * * * *

UNITED STATES PATENT AND TRADEMARK OFFICE
CERTIFICATE OF CORRECTION

PATENT NO. : 4,242,265
DATED : December 30, 1980
INVENTOR(S) : Peter C. Wade et al.

It is certified that error appears in the above-identified patent and that said Letters Patent are hereby corrected as shown below:

Column 6, line 48, "+0.49" should read -- =0.49 --.
Column 8, line 18, "3-hydroxyphenyllactic" should read --3-p-hydroxyphenyllactic--.
Column 9, lines 18 and 19, delete "room temperature (1 torr) gives a solid, m.p. 53-55°.--

Signed and Sealed this

Twenty-eighth Day of April 1981

[SEAL]

Attest:

RENE D. TEGTMEYER

Attesting Officer          Acting Commissioner of Patents and Trademarks